United States Patent
Troetzschel et al.

(10) Patent No.: US 10,679,778 B2
(45) Date of Patent: Jun. 9, 2020

(54) COMPONENT WITH A CERAMIC BASE BODY HAVING A CONDUIT AND A FASTENING ELEMENT AND METHOD

(71) Applicant: Heraeus Deutschland GmbH & Co. KG, Hanau (DE)

(72) Inventors: Jens Troetzschel, Ronneburg (DE); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 15/552,193

(22) PCT Filed: Feb. 19, 2016

(86) PCT No.: PCT/EP2016/053593
§ 371 (c)(1),
(2) Date: Aug. 18, 2017

(87) PCT Pub. No.: WO2016/131976
PCT Pub. Date: Aug. 25, 2016

(65) Prior Publication Data
US 2018/0075952 A1    Mar. 15, 2018

(30) Foreign Application Priority Data
Feb. 20, 2015   (EP) ..................... 15155989

(51) Int. Cl.
*H01B 17/30*    (2006.01)
*A61N 1/375*    (2006.01)
(Continued)

(52) U.S. Cl.
CPC ......... *H01B 17/305* (2013.01); *A61N 1/3754* (2013.01); *B22F 7/062* (2013.01);
(Continued)

(58) Field of Classification Search
CPC .................................................. H01B 17/305
(Continued)

(56) References Cited

U.S. PATENT DOCUMENTS

| 4,225,262 A | 9/1980 | Koop et al. |
| 8,659,870 B2 * | 2/2014 | Brendel .................. H01G 4/35 |
| | | 361/302 |

(Continued)

FOREIGN PATENT DOCUMENTS

| DE | 102009035971 | 2/2011 |
| DE | 102009035972 | 4/2011 |

OTHER PUBLICATIONS

Hofmann et al., Development of tough, low-density titanium-based bulk metallic glass matrix composites with tensile ductility, Dec. 23, 2008, Proceeding of the National Academy of Sciences of the USA (PNAS), vol. 105, No. 51, p. 20136. (Year: 2008).*

(Continued)

*Primary Examiner* — Stanley Tso
(74) *Attorney, Agent, or Firm* — Dicke, Billig & Czaja, PLLC

(57) ABSTRACT

One aspect relates to a component comprising
  i. a base body having a first component surface and a further component surface, the base body comprising a ceramic at least to an extent of 50 wt %, based on the total weight of the base body;
  ii. at least one electrical conduction element, the at least one electrical conduction element comprising a metal at least to an extent of 51 wt %, based on the electrical conduction element, and the at least one electrical conduction element passing through the entire base body from the first component surface to the further component surface;
  iii. at least one fastening element having a contact area, the at least one fastening element comprising a metal at least to an extent of
(Continued)

least to an extent of 51 wt %, based on the fastening element, and the fastening element being surrounded at least in part by the base body.

14 Claims, 3 Drawing Sheets

(51) Int. Cl.
| | | |
|---|---|---|
| *B22F 7/06* | (2006.01) | |
| *C22C 5/04* | (2006.01) | |
| *H02G 3/22* | (2006.01) | |
| *C22C 33/02* | (2006.01) | |
| *C22C 1/10* | (2006.01) | |
| *C22C 32/00* | (2006.01) | |
| *C22C 29/16* | (2006.01) | |
| *C22C 29/12* | (2006.01) | |

(52) U.S. Cl.
CPC ............... *C22C 5/04* (2013.01); *H02G 3/22* (2013.01); *B22F 2007/066* (2013.01); *B22F 2301/25* (2013.01); *B22F 2302/253* (2013.01); *C22C 1/1036* (2013.01); *C22C 29/12* (2013.01); *C22C 29/16* (2013.01); *C22C 32/0021* (2013.01); *C22C 32/0031* (2013.01); *C22C 33/0228* (2013.01); *C22C 2001/1073* (2013.01)

(58) Field of Classification Search
USPC ........................................................ 174/520
See application file for complete search history.

(56) References Cited

U.S. PATENT DOCUMENTS

| | | | |
|---|---|---|---|
| 9,945,749 B2 * | 4/2018 | Andreaus | ................ G01L 21/34 |
| 2003/0121952 A1 | 7/2003 | Tsukamoto | |
| 2007/0183118 A1 * | 8/2007 | Fu | ........................ A61N 1/3754 361/302 |
| 2013/0138187 A1 * | 5/2013 | Iyer | ........................ H01G 4/38 607/116 |
| 2013/0230424 A1 * | 9/2013 | Reiterer | ............... A61N 1/3754 419/8 |
| 2014/0161973 A1 | 6/2014 | Tang et al. | |
| 2014/0345934 A1 * | 11/2014 | Markham | ................ H02G 1/00 174/667 |

OTHER PUBLICATIONS

The International Search Report for International Application No. PCT/EP2016/053593 dated May 10, 2016 (3 pages).

* cited by examiner

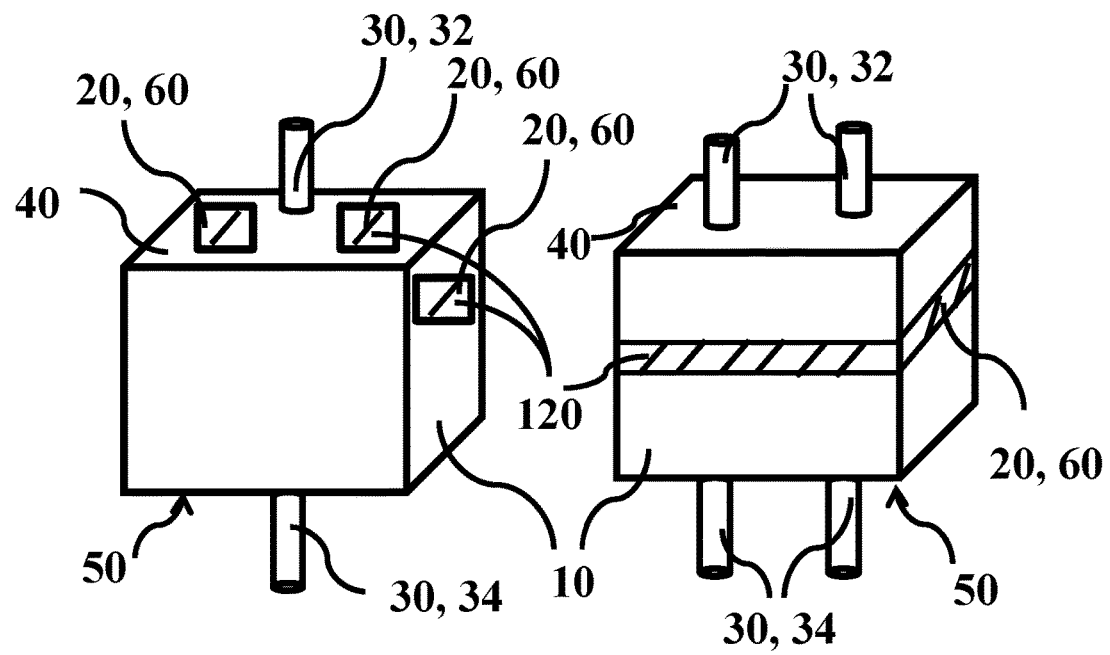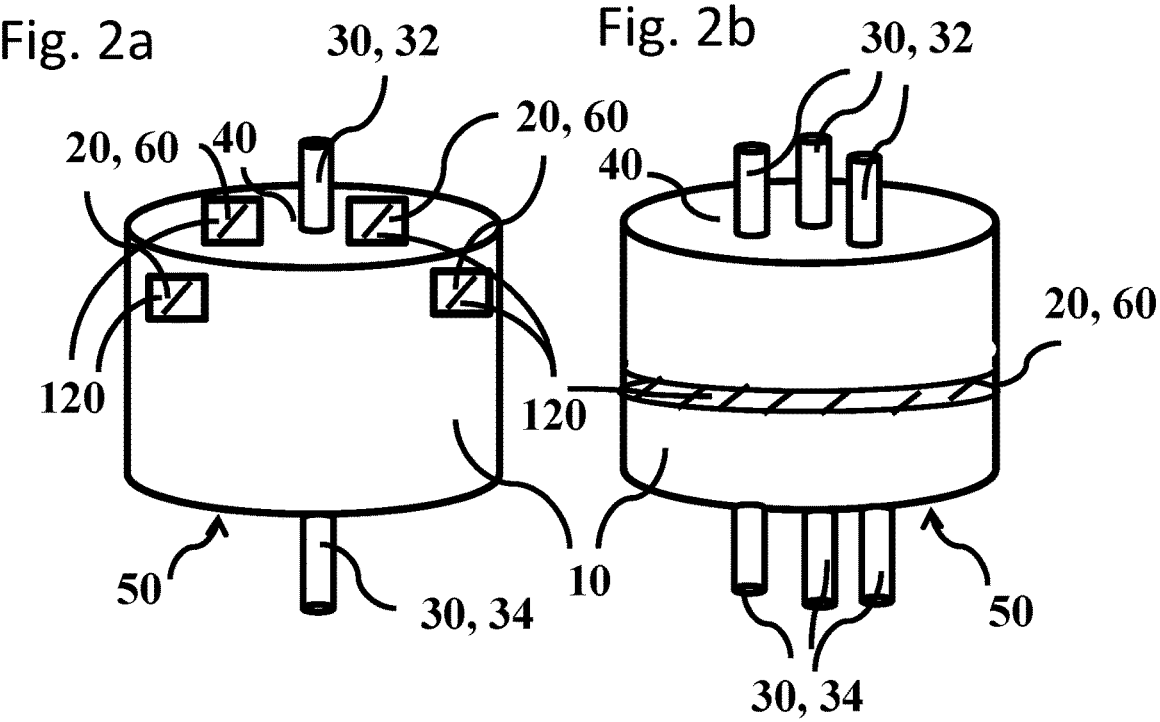

US 10,679,778 B2

COMPONENT WITH A CERAMIC BASE BODY HAVING A CONDUIT AND A FASTENING ELEMENT AND METHOD

CROSS REFERENCE TO RELATED APPLICATION

This Utility patent application claims the benefit of the filing date of European Application No. EP 15155989.5, filed Feb. 20, 2015, and International Application No. PCT/EP2016/053593, filed Feb. 19, 2016, both of which are herein incorporated by reference.

BACKGROUND

One embodiment relates to a component comprising i. a base body having a first component surface and a further component surface, the base body comprising a ceramic at least to an extent of 50 wt %, based on the total weight of the base body; ii. at least one electrical conduction element, the at least one electrical conduction element comprising a metal at least to an extent of 51 wt %, based on the electrical conduction element, and the at least one electrical conduction element passing through the entire base body from the first component surface to the further component surface; iii. at least one fastening element having a contact area, the at least one fastening element comprising a metal at least to an extent of 51 wt %, based on the fastening element, and the fastening element being surrounded at least in part by the base body.

One embodiment further relates to a device comprising a. a housing which separates an inner region from an outer region at least in part, comprising: i). a housing wall having a first housing surface facing the inner region, and a further housing surface facing the outer region of the housing; ii). at least one recess in the housing wall; b. a component of one embodiment. One embodiment also relates to a method for producing a component, with the steps of: I. providing a first composition for forming a first subregion; II. providing a further composition for forming at least one further subregion; III. providing a third composition for forming a third subregion; IV. forming a component precursor, where a first precursor for a base body is formed from the first subregion, where a further precursor for an electrical conduction element is formed from the at least one further subregion, and where a third precursor for at least one fastening element is formed from the third subregion; V. treating the component precursor at a temperature in a range from 500 to 2500° C.

Components with ceramic base body and integrated conduction element are often employed in medical apparatuses when an electrical connection is to be produced through a biocompatible material. Such components are used in particular in the therapy of heart defects, such as when cardiac pacemakers are used, for example.

Where such components are employed in, for example, a housing of a cardiac pacemaker, different requirements may be made of the material and of the connection between material and housing. One example of such a connection is shown in DE 10 2009 035 971 A1, in which a component in the form of an electrical feedthrough is provided with an annular mounting element having a passage opening in which an insulating element and a conducting wire are accommodated.

At the connection of the electrical feedthrough to a housing, a great tension in all three spatial directions is exerted on the annular mounting element of DE 10 2009 035 971 A1. This leads to very high stresses between the feedthrough and the annular mounting element surrounding it. Cracks may be developed in the feedthrough. The annular element itself may also lose its integrity, as a result of cracks or deformation, for example, or may even break.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1a illustrates a diagrammatic representation of a cube-shaped component of one embodiment having a plurality of fastening elements;

FIG. 1b illustrates a diagrammatic representation of a cube-shaped component of one embodiment having a surrounding fastening element;

FIG. 2a illustrates a diagrammatic representation of a cylindrical component of one embodiment having a plurality of fastening elements;

FIG. 2b illustrates a diagrammatic representation of a cylindrical component of one embodiment having a surrounding fastening element;

DETAILED DESCRIPTION

Figure 3:
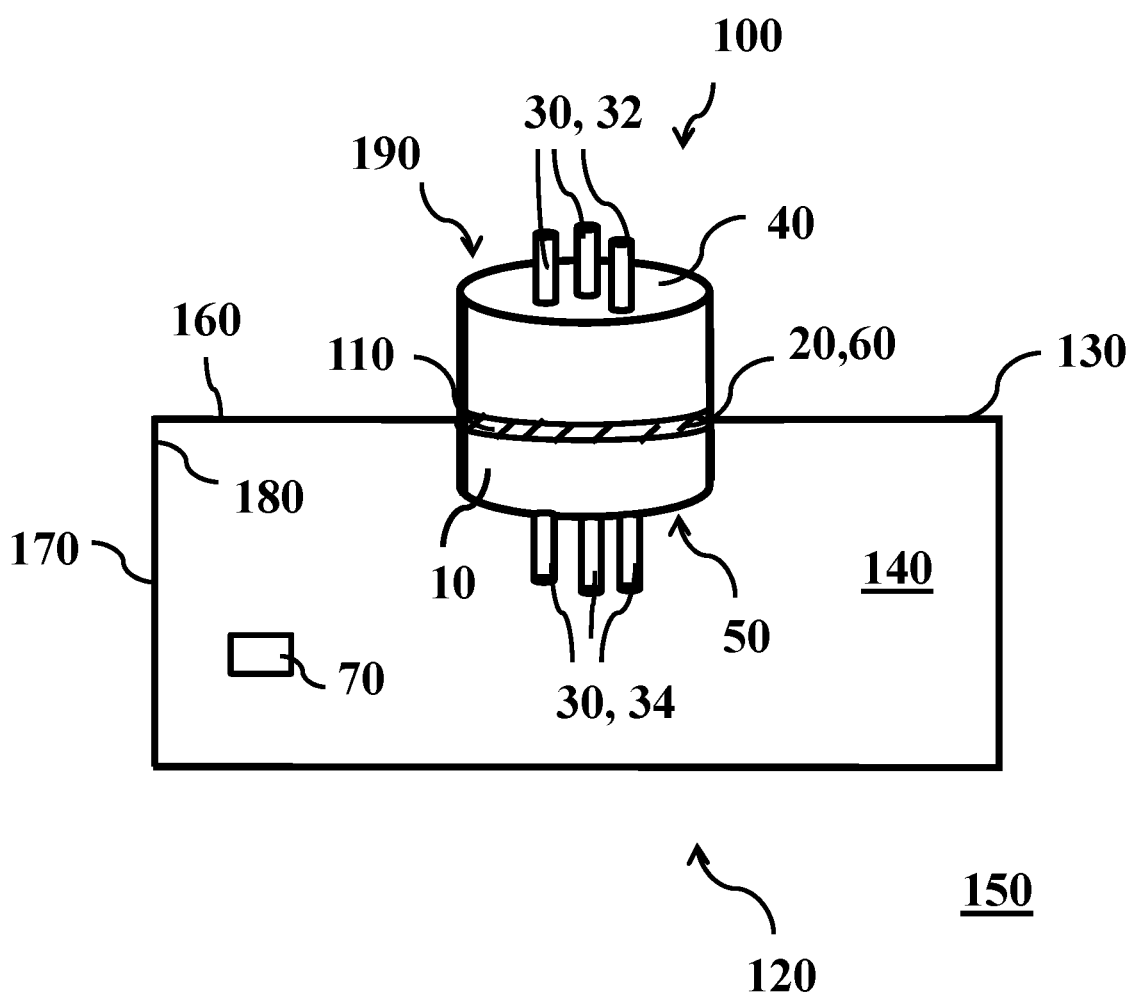
FIG. 3 illustrates a device of one embodiment with a component of one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims. It is to be understood that the features of the various exemplary embodiments described herein may be combined with each other, unless specifically noted otherwise.

Generally, an object of the present invention is to overcome at least partially the disadvantages arising from the prior art.

A further object is to provide a component which permits simple attachment to further devices without exerting excessive stress on the component or the connection.

Furthermore, it is an object to provide a component designed such that forces which occur when the component is connected to a further element, such as a housing, can be dissipated as effectively as possible.

It is a further object to provide a component which has an extremely long lifetime, particularly in acidic solutions or when subject to high pressure, or both.

It is an object, furthermore, to provide a component which can be produced inexpensively and in as few steps as possible.

A further object is to provide a device having a component which has an extremely long lifetime, particularly in acidic solutions or when subject to high pressure, or both.

Moreover, it is an object to provide a method for producing the component that is inexpensive and efficient.

Furthermore, it is an object to provide a method for producing a component that results in a component having an extremely long lifetime especially in acidic solutions or under high pressure.

Another object is to provide a device which has as far as possible a stress-free connection between the component and a housing.

A contribution to the achievement of at least one of the above-stated objects is made by the subjects of the category-forming claims. The subjects of the claims dependent from the category-forming claims represent preferred embodiments.

A first subject of the present invention is a component comprising:
 i. a base body having a first component surface and a further component surface, the base body comprising a ceramic at least to an extent of 50 wt %, based on the total weight of the base body;
 ii. at least one electrical conduction element, the at least one electrical conduction element comprising a metal at least to an extent of 51 wt %, based on the electrical conduction element, and the at least one electrical conduction element passing through the entire base body from the first component surface to the further component surface;
 iii. at least one fastening element having a contact area, the at least one fastening element comprising a metal at least to an extent of 51 wt %, based on the total weight of the fastening element;
  and the fastening element being surrounded at least in part by the base body.

The base body may comprise any component which the skilled person finds suitable for use in a component of one embodiment. Particularly if the component is to be used in a device to be implanted into a body, the component ought to comprise components which do not dissolve or alter in their form and composition in contact with body fluid. Moreover, the base body ought to consist of a material which conducts electrical current only little or not at all. The base body preferably has insulating properties with respect to the electrical conduction element fed through. The base body preferably comprises a first component selected from the group consisting of a polymer, a glass, a ceramic, a cermet, or a mixture of at least two thereof.

The polymer may be selected from the group consisting of a polyacrylate, such as polymethyl methacrylate (PMMA), a polyurethane, a polyethylene, such as polytetrafluoroethylene (PTFE), a polycarbonate, or a mixture of at least two hereof.

The ceramic may be selected from the group consisting of an oxide ceramic, a silicate ceramic, a nonoxide ceramic, or a mixture of at least two thereof.

The oxide ceramic is preferably selected from the group consisting of a metal oxide, a semimetal oxide, or a mixture thereof. The metal of the metal oxide may be selected from the group consisting of aluminum, barium, calcium, magnesium, sodium, potassium, iron, zirconium, titanium, or a mixture of at least two thereof. The metal oxide is preferably selected from the group consisting of aluminum oxide ($Al_2O_3$), magnesium oxide (MgO), zirconium oxide ($ZrO_2$), yttrium oxide ($Y_2O_3$), aluminum titanate ($Al_2TiO_5$), or a mixture of at least two hereof. The semimetal of the semimetal oxide is preferably selected from the group consisting of boron, silicon, tellurium, or a mixture of at least two thereof.

The silicate ceramic is preferably selected from the group consisting of a steatite ($Mg_3[Si_4O_{10}(OH)_2]$), cordierite (($Mg,Fe^{2+})_2(Al_2Si)[Al_2Si_4O_{18}]$), mullite ($Al_2Al_{2+2x}Si_{2-2x}O_{10-x}$ where x=oxygen vacancies per unit cell), feldspar (($Ba,Ca,Na,K,NH_4)(Al,B,Si)_4O_8$), or a mixture of at least two thereof.

The nonoxide ceramic may be selected from the group consisting of a carbide, a nitride, or a mixture thereof. The carbide may be selected from the group consisting of silicon carbide (SiC), boron carbide ($B_4C$), titanium carbide (TiC), tungsten carbide, and cementite ($Fe_3C$). The nitride may be selected from the group consisting of silicon nitride ($Si_3N_4$), aluminum nitride (AlN), silicon aluminum oxynitride (SIALON), or a mixture of at least two hereof.

The base body preferably comprises an oxide ceramic, preferably aluminum oxide ($Al_2O_3$). With further preference the base body comprises aluminum oxide in an amount in a range from 50 to 100 wt %, or preferably in a range from 70 to 100 wt %, or preferably in a range from 90 to 100 wt %, based in each case on the total weight of the base body. The particle size distribution of the base body, such as aluminum oxide, for example, is preferably $d_{20}=0.2$ μm, $d_{50}=0.4$ μm, or $d_{90}=1$ μm, or a combination of two or more of these. This means that at least 20% of the total number of particles of the base body have a diameter of 0.2 or less, or at least 50% of the particles have a diameter of 0.4 or less, or at least 90% of the particles have a diameter of 0.2 or less. Further preference is given to the combination of two or more of the aforesaid particle sizes. The particle sizes may be determined in various ways. It is preferred for optical methods to be used for this purpose, such as electrical light scattering, condensation nucleus counting, or laser diffraction. The particle size is determined preferably by means of laser diffraction, in accordance with the method elucidated in the Test Methods. The sum total of all constituents of the base body always adds up to 100 wt %.

For the purposes of one embodiment, a "cermet" is a composite material of one or more ceramic materials in at least one metallic matrix, or a composite material of one or more metallic materials in at least one ceramic matrix. To produce a cermet, for example, a mixture of at least one ceramic powder and at least one metallic powder may be used, and this mixture may be admixed, for example, with at least one binder and optionally at least one solvent. A selection for the ceramic constituents and the metallic constituents of the cermet may be made up of those specified for the base body, for the electrical conduction element or for the fastening element.

The base body of the component of one embodiment may have any shape which the skilled person would select for use in a component. The base body may, for example, have a shape selected from the group consisting of spherical, cylindrical, cuboidal, conical, pyramidal, oval, discoid, or a combination of at least two hereof. The base body is preferably designed as a cylinder.

The at least one electrical conduction element extends through at least part of the base body. The at least one electrical conduction element may have any shape which the skilled person would use for conducting electrical current through the base body. The at least one electrical conduction element preferably has a shape selected from the group consisting of filiform, cuboidal, conical, or a combination of at least two thereof. The at least one electrical conduction element preferably has an elongated shape. With further preference, the cross-sectional areas of the elongated conduction element normal to the longitudinal extent vary along the conduction element. In this context there is preferably a repeating pattern of larger and smaller cross-sectional areas. An elongated conduction element having a repeating pattern of this kind is also described as "bamboo-shaped".

The at least one electrical conduction element has a first end and a further end. Ends, so called, of the electrical conduction element are preferably regions which protrude from the base body or terminate with a plane or surface of the base body. The ends are not fully surrounded by the base body. The first end of the electrical conduction element is at least partly surrounded by the first component surface of the base body, while the other end of the electrical conduction element is surrounded at least partly by the further component surface of the base body. The component surfaces may cover areas of the base body that are different in magnitude, or else may cover areas of the same magnitude. The first and further component surfaces preferably point in different directions away from the component. With further preference the first and further component surfaces point in opposite directions away from the component. The first and further component surfaces may be separated from one another at least in part by at least one third component surface.

In one embodiment, the two ends of the at least one electrical conduction element protrude from the base body in opposite directions. Oftentimes the ends also protrude from the base body in nonopposite directions. In these cases there may be an angle formed between a longitudinal axis which passes through a first end of an electrical conduction element, and a second longitudinal axis which passes through a further end of the electrical conduction element. The angle between the longitudinal axis of the first end of the at least one electrical conduction element and the longitudinal axis of the further end of the electrical conduction element is in that case preferably in a range from 90 to 180°, or preferably in a range from 100 to 180°, or preferably in a range from 110 to 180°.

In a further embodiment, the two ends of the at least one electrical conduction element terminate with one of the outer faces, preferably both faces, of the base body. In a further preferred embodiment, two or more conduction elements run not in parallel through the base body. With preference, an angle may be formed between a first longitudinal axis which passes through a first end of an electrical conduction element, and a second longitudinal axis which passes through a further end of the electrical conduction element. The angle between the longitudinal axis of the first end of the at least one electrical conduction element and the longitudinal axis of the other end of the electrical conduction element is in that case preferably in a range from 90 to 180°, or preferably in a range from 100 to 180°, or preferably in a range from 110 to 180°.

The at least one electrical conduction element comprises at least one metal preferably in a range from 51 to 100 wt %, or preferably in a range from 60 to 100 wt %, or preferably in a range from 70 to 100 wt %, or 75 to 95 wt %, or 80 to 95 wt %, based on the total weight of the electrical conduction element.

The electrical conduction element preferably comprises at least one further component. The at least one further component may be selected from the group consisting of a ceramic, a glass, a cermet, and a polymer, or a mixture of at least two hereof. The ceramic or the polymer are preferably selected from the same group as that of the base body. The electrical conduction element in that case preferably comprises the further component in a range from 1 to 49 wt %, or preferably in a range from 3 to 40 wt %, or preferably in a range from 5 to 30 wt %, and the at least one metal in a range from 51 to 99 wt %, or preferably in a range from 60 to 97 wt %, or preferably in a range from 70 to 95 wt %, based in each case on the total weight of the at least one electrical conduction element. The sum total of all constituents of the electrical conduction element always adds up to 100 wt %.

The at least one electrical conduction element may have any shape which the skilled person would select for use in a component. The at least one electrical conduction element may be round, angular or oval in its cross-sectional area. The electrical conduction element preferably has an elongated, round shape. The electrical conduction element preferably extends with its elongated extent from the first component surface to the further component surface. Particularly if the component is joined via the fastening element to a further device, such as to a housing of a medical instrument, for example, the electrical conduction element forms an electrical conduit from the outer region of the housing to the inner region of the housing.

The at least one fastening element comprises a metal to an extent of at least 51 wt %, preferably in a range from 51 to 100 wt %, or preferably in a range from 60 to 98 wt %, or preferably in a range from 80 to 95 wt %, based in each case on the fastening element. With further preference the fastening element comprises, in a range from 1 to 49 wt %, or preferably in a range from 3 to 45 wt %, or preferably in a range from 5 to 30 wt %, based in each case on the total weight of the fastening element, a further component selected from the group consisting of a polymer, a ceramic, and a cermet, or a mixture of at least two hereof. The polymer, the ceramic or the cermet may be identical to those as described for the base body. The sum total of all constituents of the fastening element always adds up to 100 wt %.

In accordance with one embodiment, the fastening element is surrounded at least in part by the base body. In this case, at least part of the surface of the base body is in contact with part of the surface of the fastening element, and at least part of the fastening element is arranged in a recess in the base body. The area formed by the contact between base body and fastening body is referred to as the connection area. The area which is not in contact with or surrounded by the base body is referred to as the contact area. The contact area is freely accessible, for example, for contact with other elements, such as a housing of a device.

In one preferred embodiment of the component, at least 50%, preferably at least 60%, or preferably at least 70% of the surface of the at least one fastening element is surrounded by the base body. The surface of the at least one fastening element of the base body is preferably surrounded by the base body in a range from 10% to 90%, or preferably in a range from 20% to 85%, or preferably in a range from 30% to 80%.

The at least one fastening element may have any shape which the skilled person would use for a fastening element in a component of one embodiment.

The shape of the at least one fastening element is preferably selected from the group consisting of a sphere, a cuboid, a cylinder, a pyramid, a circular ring, an angular ring, an open ring, a closed ring, or a combination of at least two hereof. With further preference the at least one, and preferably all, fastening element(s) is/are designed as a cuboid. With further preference the at least one fastening element extends along at least part of the outer surface of the base body. The at least one fastening element has at least one subarea of the surface that is accessible from the outside of the component. With preference each component has at least one, more particularly two, three, four or five, fastening element(s). The volume of all fastening elements provided on a component is preferably in a range from 0.001 mm$^3$ to 5 cm$^3$, or preferably in a range from 1 mm$^3$ to 3 cm$^3$, or preferably in a range from 5 mm$^3$ to 1 cm$^3$, or very preferably in a range from 0.001 to 400 mm$^3$.

In one preferred embodiment of the component, the at least one fastening element is of annular design. The at least one annular fastening element preferably extends along the surface of the component. With further preference the at least one fastening element is arranged annularly around the base body in such a way that it subdivides the surface of the component into a first component surface and a further component surface. The at least one fastening element is preferably not in direct contact with the at least one electrical conduction element. The at least one fastening element is preferably separated from the at least one electrical conduction element by a part of the base body. According to an alternative embodiment, at least one of the fastening elements is connected to at least one electrical conduction element. With further preference this connection is located in the interior of the component.

In a further preferred embodiment of the component, the component has more than one, or preferably more than two, or preferably more than three fastening element(s). The plurality of fastening elements preferably have contact with at least an equal component surface of the component. With further preference the at least one fastening element is surrounded by the first component surface.

In one preferred embodiment of the component, the fastening element does not form a connection through the base body from the first component surface to the further component surface. The at least one fastening element preferably extends at no point through the base body of the component. The at least one fastening element is preferably in contact with at least the first or the further component surfaces.

In one preferred embodiment of the component, the base body is materially bonded to the at least one electrical conduction element and the at least one fastening element. A material bond is present when the bond can be parted only by destroying the component. Material bonds are generally achieved by sintering or by adhesive bonding of materials. Other preferred methods for producing a material bond are as follows: soldering, welding, and infiltration.

In one preferred embodiment, the component is joined to the fastening element, which is preferably a cermet, through at least one welded connection. Preferred and suitable welding methods for producing such a welded connection are laser welding or resistance welding.

In another preferred embodiment, the component is joined to the fastening element, which is preferably a cermet, through at least one soldered connection.

Infiltration refers to the formation of a material bond between at least two elements where at least one of the elements has a porous surface with open porosity, which to produce the material bond is wetted and at least partly filled out by a liquid phase. The liquid phase solidifies and in so doing produces a material bond between the first and the at least second elements. The liquid phase may be formed of liquefied material of the second element or, for the purpose of producing the material bond, it may be introduced in addition to the at least two elements. The material bond is achieved preferably through sintering.

On sintering, the physical properties of the base body transition fluidly into the physical properties of the fastening element and/or of the electrical conduction element. There is no sharp boundary between each of the regions bordering one another. Instead, there is a transition region in which the properties of the two bordering regions are mixed. This transition region is also termed a mixing region. Within this mixing region, the materials of the base body and also, at least in part, the materials of the fastening element and/or of the electrical conduction element are present alongside one another and form preferably a mixing of the materials. The materials of the two bordering regions preferably enter into connections at an atomic or molecular level.

In one preferred embodiment of the component, the ceramic of the base body is selected from the group consisting of aluminum oxide ($Al_2O_3$), zirconium dioxide ($ZrO_2$), a zirconium oxide containing an aluminum oxide (ATZ), an aluminum oxide containing a zirconium oxide (ZTA), a zirconium oxide containing an yttrium (Y-TZP), aluminum nitride (AlN), titanium nitride (TiN), magnesium oxide (MgO), a piezoceramic, barium(Zr, Ti) oxide, barium (Ce, Ti) oxide, and sodium potassium niobate, or a mixture of at least two hereof.

In one preferred embodiment of the component, the metal of the fastening element, or the metal of the electrical conduction element, or both metals is or are selected from the group consisting of palladium (Pd), platinum (Pt), gold (Au), iron (Fe), stainless steel (AISI 304, AISI 316 L), iridium (Ir), niobium (Nb), molybdenum (Mo), tungsten (W), titanium (Ti), cobalt (Co), chromium (Cr), a cobalt-chromium alloy, tantalum (Ta), and zirconium (Zr), or a mixture of at least two hereof. Within this selection, platinum is preferred.

The fastening element preferably comprises platinum in a range from 5 to 30 wt %, or preferably in a range from 10 to 20 wt %, or preferably in a range from 12 to 18 wt %, based on the total weight of the fastening element.

In one preferred embodiment of the component, the metal content of the fastening element is greater than the metal content of the electrical conduction element. The ratio of the metal content of the fastening element to the metal content of the electrical conduction element is preferably in a range from 1.1:1 to 5:1, or from 1.3:1 to 3:1, or from 1.5:1 to 3:1, the metal contents being expressed in each case in weight fractions in the element.

In another preferred embodiment of the component, the metal content of the electrical conduction element is greater than the metal content of the fastening element. The ratio of the metal content of the electrical conduction element to the metal content of the fastening element is preferably in a range from 1.1:1 to 5:1, or from 1.3:1 to 3:1, or from 1.5:1 to 2:1, the metal contents in each case being expressed in weight fractions in the element.

In one preferred embodiment of the component, the metal content of the electrical conduction element is greater than the metal content of the fastening element. With further preference the electrical conduction element comprises more metal than the fastening element in a range from 10 to 500%, or preferably in a range from 30 to 300, or preferably in a range from 50 to 200%, the percent figures being based in each case on the metal mass of the electrical conduction element.

In one preferred embodiment of the component, the component has at least one electrical conduction element. The component preferably has more than one electrical conduction element. The component preferably has more than 50, or preferably more than 100, or preferably more than 500 electrical conduction elements. With further preference the component has electrical conduction elements in a range from 2 to 1000, or preferably in a range from 5 to 500 or preferably in a range from 10 to 200, or preferably in a range from 20 to 100.

In one preferred embodiment of the component, at least a part of one of the component surfaces is biocompatible. Suitable biocompatible materials are described later on below.

A further subject of one embodiment is a device, preferably a medical device, comprising:

a. a housing which separates an inner region from an outer region at least in part, comprising:

i). a housing wall having a first housing surface facing the inner region, and a further housing surface facing the outer region of the housing;

ii). at least one recess in the housing wall;

b. a component of one embodiment as described in the first subject of one embodiment or in one of the preferred embodiments.

The device may be any device which the skilled person would use together with a component. The device is preferably a medical device. With further preference the device is suitable for being contacted with the body of a user or, preferably, inserted into the body of the user. The medical device is preferably selected from the group consisting of a therapeutic device and a diagnostic device or a combination of both.

The housing may be any housing which the skilled person would use for connection with the component. The housing preferably comprises at least one ceramic, one glass, one plastic, or one metal, more particularly one biocompatible metal. The metal is preferably selected from the group consisting of platinum, palladium, titanium, tantalum, niobium, steel, or a mixture of at least two hereof. The housing comprises the metal preferably in a range from 10 to 60 wt %, or preferably in a range from 20 to 50 wt %, or preferably in a range from 30 to 40 wt %, based on the total weight of the housing.

The housing may have any shape which the skilled person would select for the device. The housing preferably has few or no corners and edges. The shape of the housing is preferably selected from the group consisting of circular, oval, cylindrical, rectangular or a combination of at least two hereof. The volume of the device is preferably in a range from 1 to 1000 cm$^3$, or preferably in a range from 2 to 500 cm$^3$, or preferably in a range from 5 to 100 cm$^3$. With further preference the housing completely encloses the inner region together with the component.

The recess in the housing wall is preferably selected such that it is able to accommodate at least part of the component. The recess is preferably designed such that it envelops the component flush. With further preference the component is joined to the housing wall of the housing of the device in the region of the recess. The joining of the housing wall to the component takes place preferably via the at least one fastening element. Alternatively or additionally, the component or the housing may comprise further elements serving for the hermetic sealing of the component with the housing.

Thus, for example, a ring of an elastic material, such as rubber, may be installed into the recess between housing and component, and hermetically seals the device. In that case the joining of the housing to the component via the fastening elements serves only to fix the component in the recess in the housing.

With further preference, the join between the component and the housing is hermetically sealed. In one preferred embodiment of the device, the first end of the at least one electrical conduction element points to the inner region, and the other end of the at least one electrical conduction element points to the outer region, of the inner region enclosed by the housing. In this way, the hermetically sealed inner region of the housing of the device can be connected electrically to the outer region, without any possibility of liquid or gas being exchanged between inner region and outer region.

For the purposes of one embodiment, the term "hermetically sealed" means that the article under test exhibits a maximum permissible helium leakage rate of $10^{-7}$ atm*cm$^3$/sec or less by the method $A_1$ defined in MIL-STD-883G, Method 1014.13 (Status: Feb. 26, 2010), section 3.1. In one particularly advantageous version, the helium leakage rate is less than $1 \times 10^{-8}$ atm*cm$^3$/sec, more particularly less than $1 \times 10^{-9}$ atm*cm$^3$/sec. The article under test may be, for example, a component, or else a component having a hermetically sealed connection of a plurality of elements.

In one preferred embodiment of the device, the housing wall comprises at least 30 wt % of titanium, based on the total weight of the housing. With further preference the housing wall comprises titanium in a range from 30 to 100 wt %, or preferably in a range from 40 to 90 wt %, or preferably in a range from 50 to 85 wt %, based on the total weight of the housing. In a preferred embodiment of the device, the housing wall comprises an outer layer which comprises at least 30 wt % of titanium, based on the outer layer of the housing wall. The housing may comprise further components selected from the group consisting of a polymer, a ceramic, a metal, or a mixture or combination hereof. The polymer is to preferably selected from the group consisting of a polycarbonate, a polyethylene, a polyester, a polyether, a polyvinyl carbonate, a polypropylene, a polystyrene, a polyetheretherketone, a polyamine, a polyamide, a polyimine, a polyimide, a polyterephthalate, or a mixture of at least two hereof. The ceramic may be any ceramic as described for the component. The metal may be selected from the group consisting of palladium, steel, nickel, chromium, tantalum, tungsten, zirconium, iridium, titanium, niobium, or a mixture of at least two hereof.

In one preferred embodiment of the device, at least a part of the component facing the outer region, and at least the part of the housing surface facing the outer region, are biocompatible. This is especially preferred if the device is intended for implantation into a living body, such as that of a person or an animal, for example. The biocompatibility is determined according to the standard ISO 10993-4:2002.

In general, after the device of one embodiment has been implanted in a living body, the surfaces facing the inner region of the device, and the outer faces of the component, come into contact with the fluid of said body. The biocompatibility of the surfaces which come into contact with body fluid helps the body not to suffer damage on contact with these surfaces.

A further subject of one embodiment is a method for producing a component, comprising at least the following steps:

I. providing a first composition for forming a first subregion;

II. providing a further composition for forming at least one further subregion;

III. providing a third composition for forming a third subregion;

IV. forming a component precursor, where a first precursor for a base body is formed from the first subregion, a further precursor for an electrical conduction element is formed from the at least one further subregion, and a third precursor for at least one fastening element is formed from the third subregion;

V. treating the component precursor at a temperature in a range from 500 to 2300° C., preferably in a range from 600 to 2000° C., or preferably in a range from 1000 to 1800° C.;

the further precursor extending through the entire first precursor, and at least a part of the third composition being surrounded by a part of the first composition.

The first composition preferably comprises at least one first component. Furthermore, the first composition may comprise at least one further component. The first component may include any substance which contributes to the production, by heating, of a sintered product from the precursor for a component precursor.

The first component is, for example, a starting material for a sinterable substance. The first component preferably comprises a starting material for a ceramic selected from the group consisting of an oxide ceramic, a silicate ceramic, a nonoxide ceramic, or a mixture of at least two thereof. Details of the various ceramics have already been described for the component of one embodiment. Composition, form and structure as described for the component are likewise to be employed here for the product of the method for producing a component.

Furthermore, the precursor for the base body, also called base body precursor, may comprise further components. As a further component, for instance, the base body precursor may comprise any substance which the skilled person would select in order to facilitate mixing of the various components of the base body precursor. The further component preferably comprises a binder. Examples of binders are methylcellulose, 2,2,4-trimethylpentane-1,3-diol monoisobutyrate, or a mixture thereof. The methylcellulose is preferably selected from the group consisting of hydroxypropylmethylcellulose (HPMC), hydroxyethylmethylcellulose (HEMC), ethylmethylcellulose (EMC), or a mixture thereof.

Examples of further binders which can be used are thermoplastic or thermosetting polymers or waxes. They may be used alone or as mixtures of binders of two or more such components. The thermoplastic polymer may be selected from the group consisting of acrylonitrile-butadiene-styrene (ABS), polyamide (PA), polylactate (PLA), polymethyl methacrylate (PMMA), poly-carbonate (PC), polyethylene terephthalate (PET), polyethylene (PE), polypropylene (PP), polystyrene (PS), polyetheretherketone (PEEK), and polyvinyl chloride (PVC), polyvinyl butyral (PVB), or a mixture of at least two thereof. The thermosetting polymer may be selected from the group consisting of an amino resin, an epoxy resin, a phenolic resin, a polyester resin, or a mixture of at least two thereof. Waxes are hydrocarbon compounds which at room temperature are kneadable and/or solid and which above 40° C. undergo melting without decomposition. This group may include polyesters, paraffins, polyethylenes, or copolymers of at least two thereof. The precursor for the base body comprises the binder preferably in a range from 1 to 30 wt %, or preferably in a range from 3 to 25 wt %, or preferably in a range from 5 to 20 wt %, based on the total weight of the precursor for the base body. Following treatment of the component precursor, the resultant base body has the fractions of ceramic and of metal as have already been described for the base body. The sum total of all constituents of the precursor for the base body always adds up to 100 wt %.

The further precursor for the electrical conduction element preferably comprises a ceramic and a metal as have been described above for the electrical conduction element. Furthermore, the further precursor for the electrical conduction element may comprise a binder as has been described for the first precursor for the base body. The further precursor for the electrical conduction element comprises the binder preferably in a range from 1 to 30 wt %, or preferably in a range from 3 to 25 wt %, or preferably in a range from 5 to 20 wt %, based on the total weight of the precursor for the electrical conduction element. The further components, such as the ceramic and the metal, are present in the same ratio to one another as already described for the electrical conduction element. In the precursor for the electrical conduction element, their total fraction reduces in line with the use of the binder in the precursor for the electrical conduction element. Following treatment of the component precursor, the resultant electrical conduction element has the fractions of ceramic and of metal as have already been described for the electrical conduction element. The sum total of all constituents of the precursor for the electrical conduction element always adds up to 100 wt %.

The third precursor for the fastening element preferably comprises a ceramic and a metal as have been described above for the fastening element. Furthermore, the third precursor for the fastening element may comprise a binder as has been described for the first precursor for the base body. The third precursor for the fastening element comprises the binder preferably in a range from 1 to 30 wt %, or preferably in a range from 3 to 35 wt %, or preferably in a range from 5 to 20 wt %, based on the total weight of the precursor for the fastening element. The further components, such as the ceramic and the metal, are present in the same ratio to one another as already described for the fastening element. In the precursor for the fastening element, their total fraction reduces in line with the use of the binder in the precursor for the fastening element. Following treatment of the component precursor, the resultant electrical conduction element has the fractions of ceramic and of metal as have already been described for the electrical conduction element. The sum total of all constituents of the precursor for the electrical conduction element always adds up to 100 wt %.

Besides a binder, the first, the further or the third composition may also comprise at least one solvent. Examples of solvents are water, an alcohol, an amine, an acid, a hydroxide solution, or a mixture of at least two hereof. The alcohol may be selected from the group consisting of methanol, ethanol, 1-propanol, 2-propanol, 1-butanol, 2-butanol, 2-methyl-1-propanol, and 2-methyl-2-propanol, methoxypropanol, ethoxypropanol, methoxyethanol, ethoxyethanol, 4-hydroxymethyl-1,3-dioxalone, preferably methanol, ethanol, propanol, butanol, or a mixture of at least two hereof.

The amine may be selected from the group consisting of ammonia, methylamine, ethylamine, n-propylamine, isopropylamine, n-butylamine, dimethylamine, diethylamine, di-n-propylamine, di-n-butylamine, pyrrolidine, piperidine, piperazine, N-methylpiperazine, N-ethylpiperazine, morpholine, ethylenediamine, 1,2-propylenediamine, 1,3-propylenediamine, di(2-cyanoethyl)amine, di(2-aminoethyl)amine, tri(2-aminoethyl)amine, ethanolamine, diethanolamine, to triethanolamine, propanolamine, dipropanolamine, and tripropanolamine, or a mixture of at least two hereof.

The acid may be selected from the group consisting of hydrochloric acid, nitric acid, sulfuric acid, phosphoric acid, or a mixture of at least two hereof.

The hydroxide solution may be selected from the group consisting of sodium hydroxide, potassium hydroxide, lithium hydroxide, ammonium hydroxide, or a mixture of at least two hereof.

The first, further or third compositions comprise the solvent preferably in a range from 0.1 to 5 wt %, preferably in a range from 0.2 to 3 wt %, preferably in a range from 0.5 to 2 wt %, based in each case on the total weight of the first, further or third composition.

In one preferred embodiment of the method, step IV. comprises a shaping operation, preferably selected from the group consisting of a lithographic operation, injection molding, material removing, extrusion, or a combination of at least two hereof.

In a lithographic process, different layers of one or more materials are brought into a shape successively. The lithographic process corresponds preferably to a layer-by-layer screen printing process. In the screen printing process, a screen, consisting of a dimensionally most stable material such as wood; metal, preferably steel; a ceramic; or a plastic, and having a selected mesh size, is placed onto the object to be superimposed, or over the object to be superimposed. The printing compound used for application or superimposition, in the form of a paste or a powder, for example, is applied to this screen, via a nozzle or from a container, and is pressed with a squeegee through the meshes in the screen. On the basis of a pattern in the screen, different quantities of printing compound used for application or superimposition can be applied at different locations. Accordingly, through the geometry and arrangement of the meshes, it is possible either to apply a uniform film of the printing compound used for superimposition, or for regions with little or no printing compound used for application to alternate with regions having a large quantity of printing compound used for application. Preference is given to the transfer, onto the surface, of a uniform film of the printing compound used for superimposition. The screen meshes may also be partly closed by correspondingly applied materials (copying layers, screen printing stencils), so that the printing compound is transferred to the surface to be coated only in defined regions with open meshes, in order to give, for example, a defined structure such as a pattern. Furthermore, instead of screens, it is also possible to use thin films having defined openings (stencils) in order to transfer the printing compound. By repetition of this procedure using a single material or else using different materials, it is possible to obtain 3-D structures, such as the component precursor of one embodiment or parts thereof.

Injection molding is a shaping process for at least one material in order to give a shaped solid. The skilled person is aware from the prior art of different injection molding processes and also tools and conditions used in injection molding. The injection molding may be selected from the group consisting of multicomponent injection molding, powder injection molding, injection stamping, extrusion injection molding, underpressure injection molding, or a combination of at least two hereof.

Material-removing machining may be combined with any other shaping process. In material-removing machining, a solid body is structured by use of machining tools, such as a drill. In the course of the structuring, a part of the material is removed. In this way, solid bodies may be shaped into hollow bodies, for example. Through material-removing machining, for example, a cavity may be formed in the component precursor. Additionally to the material-removing machining, a polishing operation may follow.

In one preferred embodiment of the method, the component precursor is treated in step IV. at a temperature in the range from 120 to 500° C., or preferably at a temperature in the range from 150 to 450° C., or preferably at a temperature in the range from 200 to 400° C., before the treating in step V. The treating of the component precursor in step IV. and/or in step V., which is also called heating, may take place on the precursor in any way which the skilled person would select for this purpose. The heating is preferably heating by means of a technique selected from the group consisting of irradiating, heating in an oven, heating with hot gas, or a combination of at least two hereof. Irradiation may take place, for example, by IR radiation, laser radiation, UV radiation, or a combination hereof. Heating in an oven, such as a hot-air oven, for example, may take place discontinuously or continuously, for example. Heating with a hot gas may be accomplished, for example, by passing a hot gas stream such as air, nitrogen, oxygen or a mixture hereof over the applied composition. The duration of the heating in step IV. or in step V. takes place in each case preferably in a range from 0.3 to 10 h, or preferably in a range from 0.4 to 5 h, or preferably in a range from 0.5 to 3 h.

In one preferred embodiment of the method, the first composition for forming the first subregion and forming the first precursor for the base body is designed such that in the treatment step V. it shrinks by at least 1%, or preferably by at least 2%, or preferably by at least 3% more, based on the volume of the first precursor, than the further composition for forming the further precursor for the conduction element, based on the volume of the further precursor. With preference, furthermore, the third composition for forming the third subregion and forming the fastening element is designed such that in treatment step V. it shrinks by at most 5%, or preferably by at most 3%, or preferably by at most 2% more, based on the volume of the first precursor, than the first composition for forming the first precursor for the base body, based on the volume of the first precursor.

A further subject of one embodiment is a component obtainable by the method described above.

A further subject of one embodiment is a device comprising at least one component of one embodiment. The device may be, for example, a medical device, as described above.

In one preferred embodiment of the device, the device comprises at least one housing having at least one housing opening and at least one component of one embodiment, the component being connected to the housing via the at least one fastening element, and the component producing at least one electrical connection between at least one inner region of the housing and at least one outer region. As already described above, the joining of the component to the housing produces a hermetic sealing of the inner region relative to the outer region. The materials of the housing and of the component, but also the nature of the arrangement and also of the fastening of the component in the device, may be chosen and take place in the same way as already described above for the device.

Measurement Methods

1. Determination of biocompatibility:

The biocompatibility is determined according to the standard of 10993-4:2002.

2. Determination of hermetic joining:

Leakage tests are carried out with helium leakage testers and/or mass spectrometers. The standard measurement method is specified in Standard Mil-STD-883G Method 1014.13 (Status: Feb. 26, 2010). The maximum permissible helium leakage rate is specified here as a function of the internal volume of the device under test. According to MIL-STD-883G, Method 1014.13, section 3.1, method $A_1$, the maximum permissible helium leakage rate for the devices of one embodiment with housing is $10^{-7}$ atm*cm$^3$/sec. This means that the device under test (for example, the housing with component and/or the device) has a helium leakage rate of $1\times10^{-7}$ atm*cm$^3$/sec or less.

EXAMPLES

Example 1

Constitution of the First Composition

The first composition comprises 70 wt % of aluminum oxide ($Al_2O_3$) from CeramTech GmbH with a particle size of $D_{90}$=2 µm and 30 wt % of a binder METAWAX P-50 available from Zschimmer & Schwarz GmbH & Co.KG.

Example 2

Constitution of the Further Composition

The further composition comprises a mixture of 70 wt % of platinum powder from Heraeus Precious Metals GmbH & Co. KG with a particle size $D_{50}$=2 µm and also 15 wt % of aluminum oxide ($Al_2O_3$) available from CeramTech GmbH and 15 wt % of the binder METAWAX P-50 available from Zschimmer & Schwarz GmbH & Co. KG.

Example 3

Constitution of the Third Composition

The third composition comprises a mixture of 75 wt % of platinum powder from Heraeus Precious Metals GmbH & Co. KG with a particle size $D_{50}$=5 µm and also 12.5 wt % of aluminum oxide ($Al_2O_3$) available from CeramTech GmbH and 12.5 wt % of the binder METAWAX P-50 available from Zschimmer & Schwarz GmbH & Co. KG.

Example 4

Composition of the Base Body

The base body contains 100 wt % of aluminum oxide ($Al_2O_3$) from CeramTech GmbH.

Example 5

Composition of the Electrical Conduction Element

The electrical conduction element comprises 85 wt % of platinum powder from Heraeus Precious Metals GmbH & Co. KG and 15 wt % of aluminum oxide ($Al_2O_3$) from CeramTech GmbH.

Example 6

Composition of the Fastening Element

The fastening element comprises 80 wt % of platinum powder from Heraeus Precious Metals GmbH & Co. KG and 20 wt % of aluminum oxide ($Al_2O_3$) from CeramTech GmbH.

The composition of example 2 is used to produce a green cermet body of a conduction element. This is done by melting the composition of example 2 and introducing the melt into a negative mold. The negative mold is removed when the composition of example 2 has resolidified.

The composition of example 1 is used to produce a green base body for a base body functioning as an insulator. For this purpose, the composition of example 1 is melted and the melt is introduced into a negative mold, the negative mold having a hole in the interior that matches the dimensions of the green cermet body, and having a surrounding tongue for forming a groove in the outer contact area of the green base body. The negative mold is removed when the composition of example 1 has resolidified.

The composition of example 3 is used to produce a green fastening element body of a fastening element which functions as a base body frame. For this purpose, the composition of example 3 is melted and the melt is introduced into a negative mold, the negative mold having dimensions matching the groove in the contact area of the green base body. The negative mold is removed when the composition of example 3 has resolidified.

The green cermet body is inserted into the opening in the green base body. The green base body containing the green cermet body is joined via the contact area to the green fastening element body by means of tongue and groove. The component thus obtained is sintered in a chamber oven from Nabertherm GmbH at 1600° C. for 2 hours 15 minutes. The resulting sintered product was cooled in the closed oven to room temperature, by the oven being switched off, and was removed. The compositions of the individual components of the component thus obtained are listed in examples 5 to 6.

FIG. 1a shows a perspective view of a cube-shaped component 100. The component 100 has a first component surface 40 and a further component surface 50. The component 100 comprises a base body 10 with an electrical conduction element 30 passed through its interior. The electrical conduction element 30 has a first end 32 and a further end 34. The first end 32 of the electrical conduction element 30 protrudes from the first component surface 40, while the further end 34 of the electrical conduction element 30 protrudes from the further component surface 50. The electrical conduction element 30 thereby connects the first component surface 40 electrically to the further component surface 50 through the base body 10. Moreover, at various points on the surface of the base body 10, there are fastening elements 20 installed. In FIG. 1a, by way of example, two fastening elements 20 are arranged on the first component surface 40, and a further fastening element 20 is arranged on the side of the component 100 between the first component surface 40 and the second component surface 50. The fastening elements 20 all have a contact area 60 allowing them to be contacted, for example, with a housing of a device 120, as shown in FIG. 3. The contact area 60 is that part of the surface 110 of the fastening element 20 that is not surrounded by the base body 10, but is instead freely available for contacting with, for example, a housing of a device. It is also possible for fastening elements 20 to be located (not visible here) on the further component surface 50. A further embodiment having a multiplicity of fastening elements 20 would also be conceivable, together with a plurality of electrical conduction elements 30. These electrical conduction elements 30 always connect the first component surface 40 to the further component surface 50 through the base body 10. The arrangement, number, and shape of the fastening elements 20 is freely selectable.

FIG. 1b shows a component 100 having the same shape as the component 100 from FIG. 1a, with the difference that there is only one, rather than two or more, fastening element(s) 20 let partly into the base body 10. A further difference relative to the component 100 from FIG. 1a is the arrangement of a second electrical conduction element 30. Both electrical conduction elements have a first end 32, protruding from the first component surface 40, and a further end 34, protruding from the further component surface 50. The fastening element 20 likewise has a contact area 60. In this embodiment, the contact area 60 runs completely around the base body 10 of the component 100. In this example, the contact area 60 forms a ring around the base body 10.

FIG. 2a shows a component 100 having a cylindrical base body 10. Here, as likewise in FIG. 1a, a plurality of fastening elements 20 are accommodated at least in part in the base body 10 and surrounded at least in part by said base body 10. The contact area 60, however, as also in the examples from FIGS. 1a and 1b, is freely accessible. The fastening elements 20 may, as also in FIG. 1a, be located either on the first component surface or on the remaining surface of the base body 10. It is also possible for fastening elements 20 to be located (not visible here) on the further component surface 50. As in the case of the component 100 from FIG. 1a, the arrangement, number, and form of the fastening elements 20 are freely selectable.

FIG. 2b shows a component 100 having a cylindrical form and also three electrical conduction elements 30, which extend form the first component surface 40 to the further component surface 50. There may also be more or less than three electrical conduction elements 30. As in FIG. 1b, the one fastening element 20 is designed as a ring around the base body 10. In this way, a circular contact area 60 of the fastening element 20 is formed.

The fastening elements 20 from FIGS. 1a to 3b take on the function of fastening the component 100 to a further article, such as a housing of a device, for example. Furthermore, the fastening elements 20 from FIGS. 1b and 2b are additionally suitable for producing a hermetically sealed join between the component and the article.

FIG. 3 shows a device 120 of one embodiment with a component 100 of one embodiment. The component 100 of one embodiment, which is joined to the housing 130 via the contact area 60 of the fastening element 20, has, by way of example, three electrical conduction elements 30, each with a first end 32 and a further end 34. The first ends 32 point toward the outer region 150 of the device 120, while the further ends 34 point to the inner region 140 of the device 120. The component 100 is joined to the housing wall 160 of the housing 130 of the device 120 via the contact area 60 of the annular fastening element 20. To accommodate the component 100, the housing 130 has a recess 190. The component is introduced into the recess in such a way that the fastening element is joined directly to the housing wall 160, by means of welding, for example, such that a hermetically sealed join is produced between housing 130 and component 100. Particularly if the device is a medical device, such as in this case a cardiac pacemaker with a battery 70, which is to be suitable for introduction into a living body, the first surface 170, which represents the outer surface of the device, is to be biocompatible. Additionally, the base body 10 and also those parts of the electrical conduction elements 30 that may come into contact with the body are made from biocompatible material. The further housing surface 180, on the other hand, need not be manufactured from a biocompatible material, since it does not enter into contact with the body.

Figure 4:
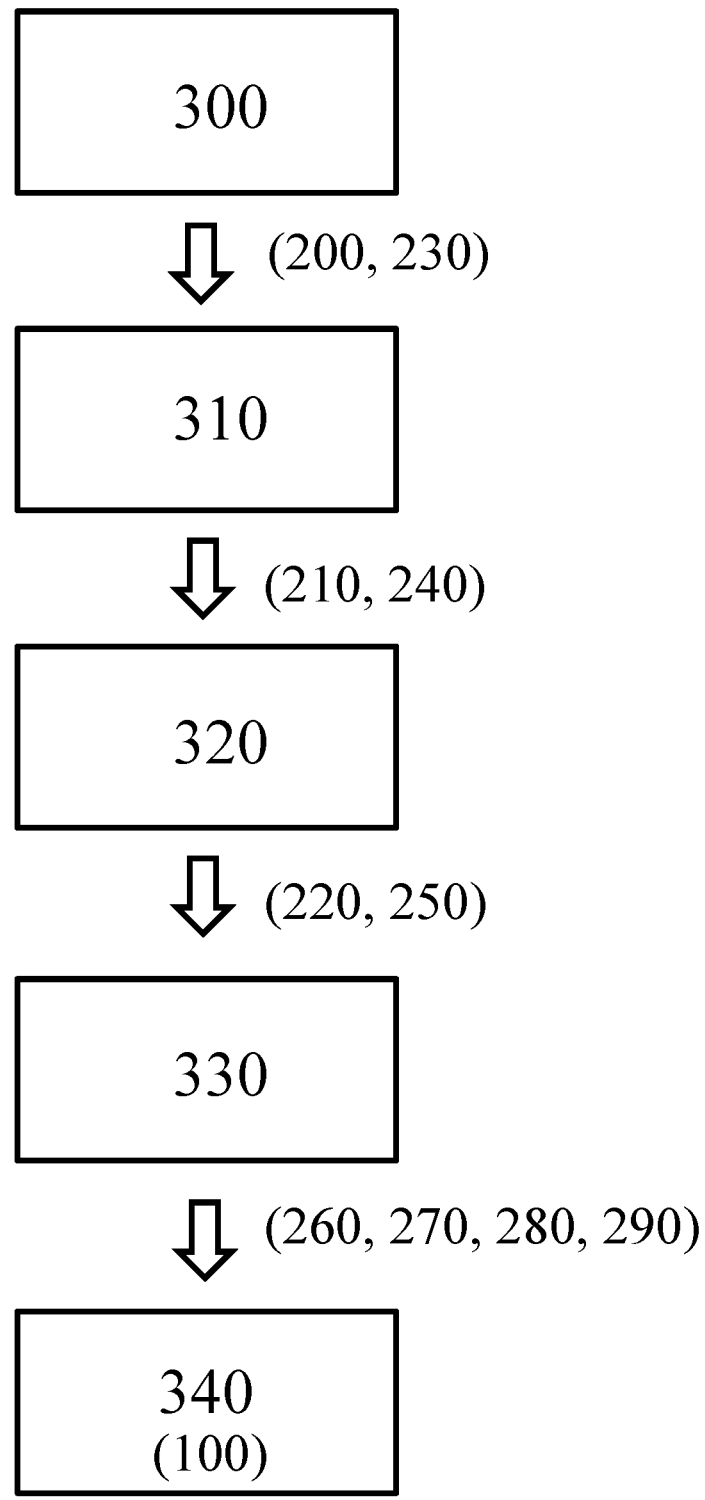
FIG. 4 illustrates a diagram of a method for producing a component of one embodiment.

FIG. 4 represents, diagrammatically, the process of the method steps of the method of one embodiment. In step I. 300, a first composition 200 is provided for forming a first subregion 230, a green base body which later forms the base body 10. The first composition 200 has, for example, the composition as specified in example 1. In a step II. 310, a further composition 210 is provided, for forming the further subregion 240, a green cermet body, which subsequently forms the at least one electrical conduction element 30. The further composition 210 has, for example, the composition specified in example 2. In a step III. 320, a third composition 220 is provided for forming a third subregion 250, a green fastening body, which will subsequently form the fastening element 20. The third composition 220 has, for example, the composition specified in example 3. Steps I. to III. may take place in succession or else simultaneously. In this example, the providing in steps I. to III. is accomplished by melting of the compositions 200, 210, and 220. In this case, the first composition 200 is poured into a first mold made from an aluminum oxide ceramic. The further composition 210 is subsequently poured into a further mold, as described for the first composition 200. The further mold has in its interior a hole which matches the dimensions of the green cermet body. Furthermore, the further mold has a surrounding tongue for modeling a groove in the outer contact area of the green base body. Similarly, the third composition 220 is poured into a third mold, as described for the first composition 200. After the compositions 200, 210, and 220 have been poured into the respective molds, they are left to rest at room temperature for at least 4 hours to solidify. This takes place in step IV. 330, with a first precursor 270 for the base body 10 being formed from the first subregion 230, a further precursor 280 for the electrical conduction element or elements 30 being formed from the further subregion 240, and a third precursor 290 for the fastening element 20 being formed from the third subregion 250. In this way, together, a component precursor 260 is formed from the subregions 230, 240, and 250.

When solidification has taken place, the respective green bodies are taken from the mold. The green cermet body is subsequently installed into the matching hole in the green base body, so that the ends of the green cermet body on both sides of the green base body are equally well accessible from both sides of the green base body. The green fastening body is introduced into the surrounding tongue of the green base body in the form of tongue and groove.

In step V. the resulting precursor for a component is sintered at 1600° C. in a chamber oven from Nabertherm GmbH for 2.25 hours. After 2.25 hours, the oven is switched off and the resulting component is left to cool to room temperature in the closed oven. The green cermet body thereby produces the electrical conduction element 20 having the composition from example 5. The base body 10 with the composition from example 4 has been formed from the green base body. The fastening element 30 having the composition from example 6 has formed from the green fastening body. The component thus formed may be utilized further, by incorporation into the housing 190 of a device 120, for example.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A component comprising:
a base body having a first component surface and a further component surface, the base body comprising a ceramic at least to an extent of 50 weight %, based on the total weight of the base body, wherein the base body comprises a recess;
at least one electrical conduction element, the at least one electrical conduction element comprising a metal at least to an extent of 51 weight %, based on the electrical conduction element, and the at least one electrical conduction element passing through the entire base body from the first component surface to the further component surface;
and at least one fastening element having a contact area, the at least one fastening element comprising a metal at least to an extent of 51 weight %, based on the total weight of the fastening element, the at least one fastening element further comprising at least one component selected from a group comprising ceramic, cermet, and polymer;
wherein the fastening element is located within the recess of the base body such that it is surrounded at least in part by the base body and such that the contact area does not extend beyond any surface of the base body;
and wherein at least 50% of the surface of the at least one fastening element is surrounded by the base body.

2. The component of claim 1, wherein the fastening element is of annular design.

3. The component of claim 1, wherein the fastening element does not form a connection through the base body from the first component surface to the further component surface.

4. The component of claim 1, wherein the base body is materially bonded to the at least one electrical conduction element and the at least one fastening element.

5. The component of claim 1, wherein the ceramic of the base body is selected from the group consisting of aluminum oxide (Al2O3), zirconium dioxide (ZrO2), a zirconium oxide containing an aluminum oxide (ATZ), an aluminum oxide containing a zirconium oxide (ZTA), a zirconium oxide containing an yttrium (Y-TZP), aluminum nitride (AlN), titanium nitride (TiN), magnesium oxide (MgO), a piezoceramic, barium(Zr, Ti) oxide, barium(Ce, Ti) oxide, and sodium potassium niobate, or a mixture of at least two hereof.

6. The component of claim 1, wherein the metal of the fastening element and/or of the electrical conduction element is selected from the group consisting of palladium (Pd), platinum (Pt), gold (Au), iron (Fe), stainless steel (AISI 304, AISI 316 L), iridium (Ir), niobium (Nb), molybdenum (Mo), tungsten (W), titanium (Ti), cobalt (Co), chromium (Cr), a cobalt-chromium alloy, tantalum (Ta), and zirconium (Zr), or a mixture of at least two hereof.

7. The component of claim 1, wherein the metal content of the fastening element is greater than the metal content of the electrical conduction element.

8. The component of claim 1, wherein the metal content of the electrical conduction element is greater than the metal content of the fastening element.

9. The component of claim 1, wherein at least part of one of the component surfaces is biocompatible.

10. A device comprising:
a housing that separates an inner region from an outer region, at least in part, comprising:
a housing wall having a first housing surface facing the inner region, and a further housing surface facing the outer region of the housing;
at least one recess in the housing wall; and
the component of claim 1.

11. The device of claim 10, wherein at least a part of the component that faces the outer region, and at least the part of the housing surface that faces the outer region, are biocompatible.

12. The device of claim 10, wherein the housing wall comprises at least 30 weight % of titanium, based on the total weight of the housing.

13. A device comprising the component of claim 1, wherein the device comprises at least one housing having at least one recess and the component of claim 1, the component being connected to the housing via the at least one fastening element, and the component producing at least one electrical connection between at least one inner region of the housing and at least one outer region.

14. A component comprising:
a base body having a first component surface and a further component surface, the base body comprising a ceramic at least to an extent of 50 weight %, based on the total weight of the base body, wherein the base body comprises a recess;
at least one electrical conduction element, the at least one electrical conduction element comprising a metal at least to an extent of 51 weight %, based on the electrical conduction element,
and the at least one electrical conduction element passing through the entire base body from the first component surface to the further component surface;
and at least one fastening element having a contact area, the at least one fastening element comprising a metal at least to an extent of 51 weight %, based on the total weight of the fastening element,
the at least one fastening element further comprising at least one component selected from a group comprising ceramic, cermet, and polymer;
wherein the fastening element is located within the recess of the base body such that it is surrounded at least in part by the base body and such that the contact area is flush with a surface transverse to the first component surface and a further component surface of the base body.

* * * * *